(12) United States Patent
Van Doorn et al.

(10) Patent No.: US 8,986,612 B2
(45) Date of Patent: Mar. 24, 2015

(54) HIFU INDUCED CAVITATION WITH REDUCED POWER THRESHOLD

(71) Applicant: Biocartis SA, Lausanne (CH)

(72) Inventors: Arie R. Van Doorn, Zaltbommel (NL); Michiel De Jong, Nuenen (NL)

(73) Assignee: Biocartis NV, Mechelen (BE)

( * ) Notice: Subject to any disclaimer, the term of this patent is extended or adjusted under 35 U.S.C. 154(b) by 0 days.

(21) Appl. No.: 14/153,352

(22) Filed: Jan. 13, 2014

(65) Prior Publication Data

US 2014/0127082 A1 May 8, 2014

Related U.S. Application Data

(60) Division of application No. 13/273,603, filed on Oct. 14, 2011, now Pat. No. 8,641,971, which is a continuation of application No. PCT/CH2010/000092, filed on Apr. 9, 2010.

(30) Foreign Application Priority Data

Apr. 14, 2009 (EP) .................................... 09157849

(51) Int. Cl.
*G01N 15/06* (2006.01)
*G01N 33/00* (2006.01)
*G01N 33/48* (2006.01)
*B01J 19/00* (2006.01)
*B01F 11/02* (2006.01)
(Continued)

(52) U.S. Cl.
CPC ........... *B01J 19/008* (2013.01); *B01F 11/0283* (2013.01); *G01N 2001/2866* (2013.01); *G01N 2035/00554* (2013.01)

USPC ............ 422/68.1; 422/50; 422/554; 422/561; 422/562; 436/43; 436/63; 436/174; 436/180

(58) Field of Classification Search
CPC ........ G01N 15/06; G01N 33/00; G01N 33/48
USPC ............. 422/50, 68.1, 554, 561, 562; 436/43, 436/63, 174, 180
See application file for complete search history.

(56) References Cited

U.S. PATENT DOCUMENTS

| 3,607,134 A | 9/1971 | McIntyre ........................ 23/292 |
| 3,633,877 A | 1/1972 | Bodine ............................ 259/72 |

(Continued)

FOREIGN PATENT DOCUMENTS

| CH | 667599 | 10/1988 | .............. B01F 15/11 |
| DE | 19820466 | 11/1999 | ................ G01N 1/28 |

(Continued)

OTHER PUBLICATIONS

International Search Report dated Nov. 16, 2010, issued in connection with PCH/2010/000092.

*Primary Examiner* — Brian J Sines
(74) *Attorney, Agent, or Firm* — Kusner & Jaffe

(57) ABSTRACT

An apparatus for irradiating a liquid sample with acoustic energy to generate cavitation in the liquid sample. The apparatus includes a source for emitting high intensity ultrasound waves and is adapted to receive a cartridge having a chamber containing the liquid sample, wherein the high intensity ultrasound waves are focused on a focus position at or near a nucleation element extending at least partially into the chamber.

19 Claims, 5 Drawing Sheets

(51) Int. Cl.
*G01N 1/28* (2006.01)
*G01N 35/00* (2006.01)

(56) References Cited

U.S. PATENT DOCUMENTS

| | | | |
|---|---|---|---|
| 4,256,697 A | 3/1981 | Baldwin | 422/104 |
| 4,371,498 A | 2/1983 | Scordato et al. | 422/102 |
| 4,571,087 A | 2/1986 | Ranney | 366/108 |
| 4,849,340 A | 7/1989 | Oberhardt | 435/13 |
| 4,857,274 A | 8/1989 | Simon | 422/72 |
| 4,857,453 A | 8/1989 | Ullman et al. | 435/7 |
| 4,874,137 A | 10/1989 | Chiba | 241/301 |
| 4,943,522 A | 7/1990 | Eisinger et al. | 435/7 |
| 4,965,047 A | 10/1990 | Hammond | 422/58 |
| 4,983,523 A | 1/1991 | Li et al. | 435/73 |
| 5,004,583 A | 4/1991 | Guruswamy et al. | 422/58 |
| 5,096,669 A | 3/1992 | Lauks et al. | 422/61 |
| 5,133,937 A | 7/1992 | Frackleton et al. | 422/81 |
| 5,147,609 A | 9/1992 | Grenner | 422/58 |
| 5,219,526 A | 6/1993 | Long | 422/64 |
| 5,229,580 A | 7/1993 | Chioniere | 219/521 |
| 5,296,374 A | 3/1994 | Culshaw et al. | 435/288 |
| 5,397,537 A | 3/1995 | Kanda et al. | 422/56 |
| 5,500,187 A | 3/1996 | Deoms et al. | 422/58 |
| 5,504,007 A | 4/1996 | Haynes | 435/285.1 |
| 5,504,013 A | 4/1996 | Senior | 436/165 |
| 5,512,159 A | 4/1996 | Yoshioka et al. | 204/403 |
| 5,578,495 A | 11/1996 | Wilks | 436/178 |
| 5,589,136 A | 12/1996 | Northrup et al. | 422/102 |
| 5,597,532 A | 1/1997 | Connolly | 422/58 |
| 5,609,822 A | 3/1997 | Carey et al. | 422/63 |
| 5,609,823 A | 3/1997 | Harttig et al. | 422/66 |
| 5,622,871 A | 4/1997 | May et al. | 436/574 |
| 5,627,041 A | 5/1997 | Shartle | 435/7.24 |
| 5,726,026 A | 3/1998 | Wilding et al. | 435/7.21 |
| 5,746,978 A | 5/1998 | Bienhaus et al. | 422/68.1 |
| 5,770,029 A | 6/1998 | Nelson et al. | 204/604 |
| 5,788,928 A | 8/1998 | Carey et al. | 422/102 |
| 5,843,680 A | 12/1998 | Manian et al. | 435/7.4 |
| 5,856,174 A | 1/1999 | Lipshultz et al. | 435/286.5 |
| 5,882,903 A | 3/1999 | Andrevski et al. | 435/91.2 |
| 5,912,134 A | 6/1999 | Shartle | 435/7.24 |
| 5,928,880 A | 7/1999 | Wilding et al. | 435/7.21 |
| 5,928,907 A | 7/1999 | Woudenberg et al. | 435/91.2 |
| 5,945,334 A | 8/1999 | Besemer et al. | 435/287.2 |
| 5,994,056 A | 11/1999 | Higuchi | 435/6 |
| 6,077,669 A | 6/2000 | Little et al. | 435/6 |
| 6,100,084 A | 8/2000 | Miles et al. | 435/306.1 |
| 6,143,573 A | 11/2000 | Rao et al. | 436/180 |
| 6,210,881 B1 | 4/2001 | Little et al. | 435/6 |
| 6,329,139 B1 | 12/2001 | Nova et al. | 435/6 |
| 6,369,893 B1 | 4/2002 | Christel et al. | 356/417 |
| 6,391,541 B1 | 5/2002 | Petersen et al. | 435/5 |
| 6,426,225 B1 | 7/2002 | Lewis et al. | 438/18 |
| 6,431,476 B1 | 8/2002 | Taylor et al. | 241/1 |
| 6,440,725 B1 | 8/2002 | Pourahmadi et al. | 435/288.5 |
| 6,521,181 B1 | 2/2003 | Northrup et al. | 422/52 |
| 6,524,532 B1 | 2/2003 | Northrup | 422/52 |
| 6,551,817 B2 | 4/2003 | Besemer et al. | 435/287.2 |
| 6,565,815 B1 | 5/2003 | Chang et al. | 422/198 |
| 6,664,104 B2 | 12/2003 | Pourahmadi et al. | 435/288.6 |
| 6,699,711 B1 | 3/2004 | Hahn et al. | 435/283.1 |
| 6,713,297 B2 | 3/2004 | McMillan et al. | 435/283.1 |
| 6,783,736 B1 | 8/2004 | Taylor et al. | 422/103 |
| 6,818,185 B1 | 11/2004 | Petersen et al. | 422/102 |
| 6,878,540 B2 | 4/2005 | Pourahmadi et al. | 435/287.2 |
| 6,881,541 B2 | 4/2005 | Petersen et al. | 435/6 |
| 6,887,693 B2 | 5/2005 | McMillan et al. | 435/173.7 |
| 6,893,879 B2 | 5/2005 | Petersen et al. | 436/178 |
| 6,987,018 B2 | 1/2006 | Taylor et al. | 435/286.7 |
| 7,188,001 B2 | 3/2007 | Young et al. | 700/266 |
| 7,569,346 B2 | 8/2009 | Petersen et al. | 435/6 |
| 2002/0019060 A1 | 2/2002 | Petersen et al. | 436/514 |
| 2002/0084329 A1 | 7/2002 | Kaye et al. | 235/462.01 |
| 2004/0200909 A1 | 10/2004 | McMillan et al. | |
| 2005/0042137 A1 | 2/2005 | Petersen et al. | 422/58 |
| 2006/0019379 A1 | 1/2006 | Taylor et al. | 435/306.1 |
| 2006/0027686 A1 | 2/2006 | Taylor et al. | 241/2 |
| 2006/0030038 A1 | 2/2006 | Taylor et al. | 435/306.1 |
| 2006/0158956 A1 | 7/2006 | Laugharn, Jr. et al. | 366/127 |
| 2008/0031094 A1 | 2/2008 | Laugharn, Jr. et al. | 367/138 |
| 2008/0057572 A1 | 3/2008 | Petersen et al. | 435/306.1 |
| 2010/0068706 A1 | 3/2010 | Pourahmadi et al. | 435/6 |

FOREIGN PATENT DOCUMENTS

| | | | |
|---|---|---|---|
| EP | 0337690 | 10/1989 | C12Q 1/68 |
| EP | 0353365 | 7/1990 | C12N 1/06 |
| EP | 0512334 | 11/1992 | C12Q 1/68 |
| EP | 0271448 | 6/1998 | B01J 19/10 |
| EP | 0757830 | 12/1998 | G09F 3/00 |
| EP | 0706649 | 1/2001 | G01N 21/64 |
| EP | 1383602 | 6/2006 | B01L 3/02 |
| EP | 1181098 | 7/2006 | B01L 3/00 |
| EP | 0915173 | 1/2007 | C12Q 1/68 |
| EP | 1179585 | 7/2008 | B01J 19/00 |
| GB | 938163 | 10/1963 | |
| JP | 2007-10345 | 1/2007 | B01F 11/02 |
| WO | WO 95/11454 | 4/1995 | G01N 33/50 |
| WO | WO 95/29473 | 11/1995 | G09F 3/00 |
| WO | WO 98/38487 | 9/1998 | G01N 1/31 |
| WO | WO 99/58637 | 11/1999 | C12M 1/42 |
| WO | WO 2006/136990 | 12/2006 | B01L 3/00 |
| WO | WO 2010/064160 | 6/2010 | B01L 7/00 |

HIFU INDUCED CAVITATION WITH REDUCED POWER THRESHOLD

RELATED APPLICATIONS

This application is a divisional of U.S. application Ser. No. 13/273,603, filed Oct. 14, 2011, which is a continuation of International Application Ser. No. PCT/CH2010/000092, filed Apr. 9, 2010, which claims the benefit under 35 U.S.C. §119(a) of European Patent Application No. 09157849.2, filed Apr. 14, 2009, said applications fully incorporated herein by reference.

FIELD OF THE INVENTION

The present disclosure relates to acoustical devices for inducing cavitation. In particular the present disclosure relates to an apparatus for irradiating a sample with acoustic energy to generate cavitation in the liquid sample, a cartridge for an apparatus for irradiating a liquid sample with a acoustic energy to generate cavitation in the liquid sample, a system for irradiating a liquid sample with acoustic energy, a computer program element, a computer readable medium and a method for irradiating a liquid sample with acoustic energy to generate cavitation in the liquid sample.

BACKGROUND OF THE INVENTION

High-intensity focused ultrasound (HIFU) has been increasingly used in the field of molecular device applications to overcome problems of known technologies of treating samples. By means of the acoustic energy focused onto the sample sonophysical or sonochemical reactions can be caused in an efficient way. Furthermore in recent years, progress in many aspects of sample-in result-out devices, also known as micro total analysis systems or lab on a chip has been realized. For example the integration and miniaturization results in systems requiring a relative small, acceptable contamination risk of the sample, high sensitivity and short turnaround time of the test and lower costs per tests. Furthermore between sample input and result generation minimal operator intervention shall be required. Operator interventions can be done by relatively unskilled operators and moderate demands on operating environment.

Cavitation is defined as the phenomenon of formation of vapor bubbles of a liquid inner region when the pressure of the liquid falls below its vapor pressure. In molecular analyzing devices cavitation may be used to achieve lysis of cells within the sample that is to be treated with HIFU but also other treatment functions like mixing liquefaction may be caused by HIFU. Within known technologies the treatment functionalities mixing and lysing require different power levels, which may make it complicate to do both in one single chamber. To provide for high power systems large transducers are used and liquid cooling may be applied in order to avoid excessive heating.

SUMMARY OF THE INVENTION

It may be an object of the present disclosure to provide a HIFU sample treatment with reduced power.

It shall be noted that in the context of the present disclosure the following definitions and abbreviations will be used:

High Intensity Focused Ultrasound (HIFU): The term "HIFU" will be used in the context of the present disclosure as focused acoustic field with source frequencies in the range of 0.2 MHz to 10 Mhz, with amplitudes chosen to be sufficient efficient to create high pressure shock-waves and/or cavitation in the focal zone. Focal zone dimensions (length and diameter) are dependent on the source transducer type (e.g. natural focusing by flat or enforced focusing by conical/spherical source transducers). Exemplary length-scales for the indicated frequency range are (sub) millimeters.

Sample-in result-out system: A system which accepts a (e.g. biological) sample, does all the required preparation steps to prepare for detecting any kind of facts, runs the detection and delivers the detection results. For example a device for molecular analysis of samples like e.g. blood or other cells can be provided, that provides for all necessary analysis steps from the supply of the natural, untreated sample to the result of the analysis.

Interface/Interface medium: In the context of the present disclosure the propagation path of the acoustic energy may consist of several components like the source, the full solid coupler and the cartridge. In order to describe the transitions or areas where these different elements of the propagation path get in physical contact to each other the terms interface and interface medium are used. For example if a coupler is physically contacted with the cartridge, the interface medium of the coupler describes the material used in the coupler within this area of the coupler brought in contact with the cartridge.

Apparatus/Device: The expression "device" in the context of the present disclosure includes molecular diagnostic devices as well as other devices. Applications of the device may e.g. be in healthcare/life science, food industry, veterinary practice and forensic applications.

Sample: It shall explicitly be noted that the term "sample" may contain samples for molecular analysis being treated with the device according to the present disclosure. For example blood, cultured blood, urine, aspirate, samples with water like viscosity, heterogeneous samples or samples on a carrier like BAL, sputum, tracheal aspirate, CSF, swab and/or brush with pathogen. Nevertheless this does not mean that any other kind of matter, solid, liquid, gaseous or any combination thereof is excluded from being a sample and being irradiated with focused acoustic energy by the present disclosure.

Treatment of the sample: The term "treatment" or "treating" is used in the context of the present disclosure to describe the interaction of the focused acoustic energy with the sample. By the HIFU the various sonochemical and/or sonophysical reactions are caused in the sample to generate functionalities like e.g. mixing, dispersing, stirring, elution from swabs or brushes, liquefaction, lysing or cell release.

According to an exemplary embodiment of the present disclosure an apparatus for irradiating a liquid sample with acoustic energy to generate cavitation in the liquid sample is presented. The apparatus comprises a source for emitting high intensity ultrasound waves. Furthermore the apparatus is adapted for receiving a cartridge. For example the apparatus comprises a receiving section for receiving a cartridge. The cartridge contains the liquid sample and a liquid air interface. Furthermore the apparatus focuses the high intensity ultrasound waves such that a fountain of liquid above the liquid-air interface within the cartridge is created when the cartridge is received by the apparatus e.g. by the receiving section.

In other words the apparatus is combined with a cartridge, that is not a flow-through cartridge, but provides firstly for the liquid sample and secondly for an air volume above the liquid sample. Thus the boundary layer between the liquid sample and the air volume is present within the cartridge. The apparatus is furthermore adapted for receiving the cartridge at the receiving section in order to build up a propagation path for the high intensity ultrasound waves from the source to the cartridge and therefore to the liquid sample.

The focusing which creates the fountain may be realized in various different ways. For example the apparatus may focus direct onto the liquid-air interface but may also focus below that interface into the liquid sample or above that interface and may thus focus into the air volume that is provided by the cartridge above the liquid air interface. All these embodiments may be subsumed under the term "focusing on the liquid-air interface". An important aspect of all possible focusing possibilities is that a fountain is created. Fountain droplets returning from the fountain to the liquid sample may induce a cavitation process within the liquid sample. The droplets returning into the liquid may introduce small air bubbles and/or air films which in turn may be the starting point for a cavitation. To be more precise exemplary embodiments of the focusing shall be described in detail hereinafter:

As a first exemplary embodiment of the focusing the case in which the focal length of the source and/or possible focusing elements like e.g. lenses is longer than the distance from the source to the liquid-air interface the imaginary focus point is above the liquid-air interface and thus in the air volume in the cartridge. For this condition a fountain formation may be easy to achieve. In this case a certain amount of the HIFU waves propagating from the source to the liquid-air interface are not transmitted into the air volume above this interface but are back reflected into the sample. Thereby the back reflected HIFU waves are more or less focused onto the liquid-air interface. It shall explicitly be noted that this way of focusing, namely providing for an imaginary focal region or an imaginary focal spot in the air volume above the liquid-air interface, shall be comprised when describing the present disclosure. The focusing is done via the back reflection at the liquid-air interface as described above. An important aspect of the present disclosure is that the apparatus focuses the HIFU waves onto the liquid-air interface in such a way, that the fountain is created. This may reduce the power threshold required for cavitation.

Of course a direct and explicit focusing of the HIFU waves onto the liquid air interface is possible as a second exemplary embodiment of the focusing of the HIFU waves by the apparatus. This may also create a fountain reducing the power threshold. As the apparatus focuses the emitted HIFU waves on the liquid air interface with sufficiently high power a fountain is created in the focal zone of the focused HIFU waves.

A third exemplary embodiment of the focusing of the HIFU waves by the apparatus shall be described hereinafter: In the case that the focal length of the source and/or possible focusing elements like e.g. lenses is shorter than the length from the source to liquid-air interface the focus point or focal spot may be in the sample liquid. It may be an exemplary distance from the focal spot or focal zone to the liquid-air interface that ranges between 1-2 cm, wherein the focal zone is below the liquid-air interface inside the liquid in the cartridge. Thereby an important aspect is that this focusing having the focal spot slightly below the liquid-air interface creates a fountain and thus reduces the power threshold required for cavitation in the sample.

Furthermore it shall explicitly be noted that the term focal length shall not be misleading, because it suggests a point focus. In reality the focus shape may range form a point to a cylinder-like (for a weakly-focusing curved source or a natural-focusing flat source). It is important to note that with weakly focusing or weakly focusing sources fountains may be formed over a much larger range of fluid heights. It should also be noticed that for larger source input powers the distance to the liquid-air interface, which is the liquid surface may be increased which enables a larger volume in the cartridge to be treated or processed by the HIFU waves.

In other words an apparatus for molecular diagnostics is presented to provide for cavitation with a reduced power threshold. The returning droplets of the fountain created by the focused HIFU waves thus act as nucleation features within the sample. In other words this exemplary embodiment of the present disclosure does not use homogeneous cavitation as known technologies may do. This exemplary embodiment of the present disclosure uses heterogeneous cavitation as the cavitation within the liquid sample is induced by the apparatus by creating the fountain due to the focusing.

In other words this exemplary embodiment of the present disclosure avoids to induce cavitation via the wall of a chamber of the cartridge.

The fact that the apparatus focuses in such a way that a fountain is caused which fountain in turn causes droplets falling back to the liquid as nucleation elements leading to a reduced power which is necessary for generating cavitation in the liquid sample. In other words the focusing of the HIFU waves during for example treatment, pretreatment or lysis of the liquid sample leads to the possibility to use HIFU waves with a reduced energy and power. This may lead to the advantages of being able to use smaller transducers or sources. Also a liquid cooling may be avoided, as heating due to absorption of the HIFU waves can also be reduced as the use of reduced power may be possible. Furthermore the possibility is created to use coupling media and transfer media for the HIFU waves that are solid state materials. That means that the HIFU waves may be transferred across dry interfaces when propagating from the source to the sample. This may also be possible due to the power reduction of the used HIFU waves, as also the absorption within these media is reduced to a value that does not lead to melting and/or degradation.

Furthermore a higher degree of miniaturization may be reached due the possibility to use smaller transducers or sources and the complexity of the apparatus may further be decreased. In addition to that it may be possible to use polymer based materials as cartridge materials, as the absorption of HIFU waves by the cartridge may be reduced by being able to use HIFU waves with reduced power.

This means, that the cartridge may be formed out of a material chosen from the group comprising polyethylene, polypropylene, polyethylene terephthalate, polymethylpentene, polymethylmethacrylate, polycarbonate, polystyrene, a polymer based material, and any combination thereof. In addition to that the cartridge may have one of the following characteristics: disposable, consumable, removable, may contain one chamber or a lot of chambers, may contain one sample or a lot of samples, industrial applicable.

These before mentioned advantages may lead to a cost reduction of the apparatus, and a miniaturization of the apparatus and/or the cartridge. Furthermore a contamination risk of the sample with liquids from a cooling bath is avoided, as no cooling bath may be needed anymore.

Furthermore it shall be noted that for lysing cells that are present in the liquid sample cavitation may be required. By reducing the minimum power necessary for generating cavitation as described above the apparatus now enables to use one apparatus setup with a relatively small source using reduced power values with which mixing and lysis may be done.

As the minimum power necessary for generating cavitation in the liquid sample is reduced by the apparatus mixing and lysis can be done in a cartridge made out of a polymeric material like for example polyethylene, epoxy and silicon. Melting and/or degradation of the cartridge may be avoided by this exemplary embodiment of the present disclosure as the used power may be reduced. Therefore a polymer based process chamber being the cartridge may be part of a complete sample-in result-out system using consumable cartridges. This may reduce the costs of measurements being performed at the sample.

In other words this exemplary embodiment of the present disclosure overcomes the disadvantage of known technologies that the wall of the cartridge or the process chamber combines two functions, firstly a containment of the liquid sample and secondly the induction of cavitation. Contrary to these known technologies in this exemplary embodiment of the present disclosure the containment of the liquid sample and the induction of cavitation in the liquid sample are embodied separately. The containment is embodied by the chamber and the induction of cavitation is caused due to the focusing on the liquid air interface that causes a fountain reducing the power threshold for cavitation induction.

It shall explicitly be noted that in any embodiment of the present disclosure the set in of cavitation may be dependent from the power of the HIFU source.

Furthermore the apparatus may be adapted in such a way, that when the apparatus is turned on, the apparatus automatically adjusts several different parameters in such a way, that the fountain is created. Exemplary parameters may for example be the power of the source, the focal spot position and/or the shape of the focal spot.

According to another exemplary embodiment of the present disclosure a nucleation element for reducing a minimum power necessary for generating cavitation in the liquid sample is comprised by the apparatus and wherein a droplet of the fountain falling back from the fountain onto the liquid sample is the nucleation element.

An important aspect of all possible focusing possibilities is that a fountain is created. Fountain droplets returning from the fountain to the liquid sample may induce a cavitation process within the liquid sample. The droplets returning into the liquid may introduce small air bubbles and/or air films which in turn may be the starting point for a cavitation.

According to another exemplary embodiment of the present disclosure a control unit for controlling a focus position of the high intensity ultrasound waves is comprised by the apparatus.

The control unit may for example position the apparatus with respect to the cartridge and may therefore control a three dimensional positioning system, which may also be comprised by the apparatus. The positioning system may also position the position of the cartridge. Thereby an important aspect of the focus position is that when cavitation within the liquid sample is required for e.g. using cells, the focus position is placed at the liquid air interface as described above.

Thereby it shall explicitly be noted that the formation of the fountain may be dependent on the geometry of the focal spot of the used high intensity ultrasound waves. It may also be dependent on the HIFU power.

Thereby the fountain is created by the HIFU waves in such a way, that parts of the liquid sample are pushed up or transported out of the liquid sample into the volume of air above the liquid sample. In other words the cartridge is adapted in such a way that it provides for a minimum height of an air volume within the cartridge above the liquid air interface wherein the minimum height of the air volume allows a development of the fountain reducing the power threshold.

According to another exemplary embodiment of the present disclosure the apparatus is adapted for lysing cells within the liquid sample by the cavitation.

In other words by irradiating the liquid sample with high intensity ultrasound waves a pretreatment also lysing of the sample or components of the sample can be done with one and the same apparatus and with one and the same cartridge, thereby pretreating the liquid with the high intensity ultrasound waves wherein pretreating is accomplished with a method selected from the group comprising mixing with the reagent, circulation, release of a cell, pathogen and matrix of a swab, affection, incubation of the liquid with a reagent at room temperature or elevated temperature, shaking, mixing, steering, extracting and nucleic acid extracting, flow generation, liquid homogenation, separating by centrifuging, and any combination thereof. In other words between the two steps of mixing and lysing an increase of power of the source may be avoided by this exemplary embodiment of the present disclosure.

According to another exemplary embodiment of the present disclosure the receiving of the cartridge by the apparatus provides for a complete dry coupling of the high intensity ultrasound waves between the apparatus and the cartridge when the cartridge is inserted into the receiving section. For example a receiving section may be comprised in the apparatus to provide for such a dry coupling.

In other words it may be possible to provide for a propagation path for the HIFU waves that partially comprises liquid material and partially comprises solid state materials. For example a flexible foil may be used to build an interface medium between a liquid coupling medium and the cartridge which may be made out of a polymer. This exemplary embodiment of the present disclosure combines the advantage of a liquid coupler having low attenuation acoustical properties and the elasticity of the foil being adaptable to the shape of the polymer based cartridge to achieve an efficient coupling of the HIFU waves to the cartridge and sample. In addition to that the outer surface of the apparatus is completely dry and the foil completely envelopes the liquid. Therefore contamination risks may be reduced. Furthermore, in case of a leakage of the cartridge this leakage may be detected very fast as the presence of liquid from the coupling medium can be excluded as it is enveloped.

According to another exemplary embodiment of the present disclosure the apparatus further comprises a full solid coupler for at least partially transferring the high intensity ultrasound waves from the source to the cartridge when the cartridge received by the apparatus. For example the receiving section of the apparatus may receive the cartridge.

In other words this exemplary embodiment of the present disclosure makes it possible to completely use solid state materials for transferring the HIFU waves from the source to the sample. Therefore contamination risks of liquid couplers and the sample is avoided, as any coupling liquid is avoided. In case of a leaking cartridge it can unambiguously be detected because no liquid for coupling is present. This may be a facilitation of measurements done with the apparatus. Furthermore this may reduce the costs of the measurements done with the apparatus.

According to another exemplary embodiment of the present disclosure the apparatus further comprises at least one of: an extraction unit, a nucleic acid amplification unit, a reagent storage unit, a detection unit for measuring a physical parameter of the liquid sample wherein the apparatus is adapted for analyzing the liquid sample based on the detected physical parameter. According to this embodiment the apparatus may comprise, for instance: an extraction unit; an extraction unit and a nucleic acid amplification unit; an extraction unit, a nucleic acid amplification unit, and a detection unit. In each of these options a reagent storage unit may be present in addition to the elements of each option listed in the previous sentence. The extraction unit allows a nucleic acid to be obtained from a sample processed by the apparatus. The nucleic acid amplification unit allows a nucleic acid obtained from the sample to be amplified (using, for instance, PCR). The reagent storage unit comprises a reagent needed for, for instance, extraction and/or amplification.

In other words this exemplary embodiment of the present disclosure is a complete sample-in answer-out system in which a sample may be firstly pretreated, secondly a lysis process step may be applied to the sample by the apparatus and thirdly for example an optical measurement may be done with the detection unit. In addition to that a processing unit may process the data delivered by the detection unit and may provide for measuring results that may be output to a user.

Furthermore an excitation unit for exciting the liquid sample for the analyzing step e.g. may be comprised by the apparatus; for example a laser, a mechanical stirrer, or electrical components causing an electrical current in the liquid sample.

Additionally the apparatus may have a lens for focusing the HIFU waves. The lens may also be part of the cartridge.

According to another exemplary embodiment of the present disclosure a system for irradiating a liquid sample with acoustic energy to generate cavitation in the liquid sample is presented wherein the system comprises an apparatus according to one of the before mentioned embodiments and a cartridge for containing the liquid sample.

According to another exemplary embodiment of the present disclosure a method for irradiating a sample with acoustic energy to generate cavitation in the liquid sample is presented. Thereby the method comprises the steps providing for a source for emitting high intensity ultrasound waves, providing for a cartridge containing the liquid sample and a liquid air interface within the cartridge and focusing the emitted high intensity ultrasound waves on the liquid air interface within the cartridge.

According to another exemplary embodiment of the present disclosure the method further comprises the steps of creating a fountain of liquid within the cartridge and inducing a cavitation process in the liquid sample by droplets of the fountain.

In clear contrast to homogeneous cavitation used in known technologies this method provides for heterogeneous HIFU induced cavitation with a reduced power threshold.

According to another exemplary embodiment of the present disclosure a computer program element is presented wherein the element is characterized by being adapted when in use on a computer to cause the computer to perform the steps emitting high intensity ultrasound waves from a source and focusing the emitted high intensity ultrasound waves on a liquid air interface within a cartridge containing a liquid sample for inducing cavitation within the liquid sample.

In another exemplary embodiment of the present disclosure a computer readable medium is presented wherein the computer readable medium has a computer program element according to the before mentioned embodiment stored on that.

According to a further embodiment of the present disclosure a medium for making a computer program element available for downloading, which computer program element is arranged to perform the method according to one previously described embodiment of the present disclosure.

According to another exemplary embodiment of the present disclosure a cartridge for an apparatus for irradiating a liquid sample with acoustic energy to generate cavitation in the liquid sample is presented, the cartridge comprising a chamber for containing the liquid and a nucleation element fixed at the chamber.

It shall explicitly be noted, that this exemplary embodiment may be realized independently from the focusing onto the liquid-air interface and may be realized independently from the creation of a fountain. Thus this protruding nucleation element, which may be e.g. a ceramic rod or e.g. an alumina contrary to the fountain creation no air gap may be required for this exemplary embodiment of the present disclosure.

A rough surface of the nucleation element itself may now be the source of small air-bubbles, which in turn are acting as nucleation sites.

In other words the cartridge introduces cavitation enhancing means into the liquid sample being contained in the chamber. By introducing these cavitation enhancing means in or near the focal zone a reduction of the power threshold needed to induce cavitation may be achieved by an order of magnitude. Thereby the focal zone may not be into contact with the wall of a chamber. It shall explicitly be noted, that the before mentioned advantages of the apparatus similarly pertain to this exemplary embodiment of the present disclosure.

Thereby a material for the nucleation element may be used having a specific rough surface characteristic. Furthermore material may be used that resists the HIFU wave power in or near the focal area sufficiently long in order to meet a test done by an apparatus with this cartridge. For example a ceramic rod or an element out of aluminum may efficiently induce cavitation.

According to another exemplary embodiment of the present disclosure cartridge comprises a protrusion element to fix the nucleation element at the cartridge.

It shall explicitly be noted, that this exemplary embodiment may be realized independently from the focusing onto the liquid-air interface and may be realized independently from the creation of a fountain.

Thereby the protrusion element may be any kind of device that is adapted to fix or arrange a nucleation element within the cartridge in such a way a fixed nucleation element like for example a ceramic rod is positioned at the focal position within the liquid sample. This may be seen in FIGS. 8 and 9 in a detailed manner.

According to another exemplary embodiment of the present disclosure a system for irradiating a liquid sample with acoustic energy to generate cavitation in the liquid sample is presented. The system comprises an apparatus wherein the apparatus comprises a source for emitting high intensity ultrasound waves. Furthermore the apparatus is adapted for receiving a cartridge. For example the apparatus may comprise a receiving section. The system further comprises a cartridge according to one of the two before mentioned cartridge embodiments. Thereby the cartridge contains the liquid sample and the apparatus focuses the high intensity ultrasound waves on the nucleation element when the cartridge is received by the apparatus.

According to another exemplary embodiment of the present disclosure an apparatus for irradiating a liquid sample with acoustic energy to generate cavitation in the liquid sample is presented. The apparatus comprises a source for emitting high intensity ultrasound waves. The apparatus is adapted for receiving a cartridge, the cartridge containing the liquid sample, and—with the cartridge being received by the apparatus—the apparatus is adapted for focusing the high intensity ultrasound waves on a nucleation element in the cartridge.

As also for these embodiments of the present disclosure the minimum power necessary for generating cavitation in the liquid sample is reduced by inserting a nucleation element a partially dry coupling or also a complete dry coupling using only solid state materials is possible with such a system. Details and advantages of such a dry coupling and a dry coupling completely using solid state materials are also described above.

The described embodiments similarly pertain to the apparatus, the system, the method, the computer program element, the computer readable medium, and the cartridge. Synergetic effects may arise from different combinations of the embodiments although they might not be described in detail.

Further on it shall be noted that all embodiments of the present disclosure concerning a method might be carried out with the order of the steps as described, nevertheless this has not to be the only essential order of the steps of the method all different orders of orders and combinations of the method steps are herewith described. The aspects defined above and further aspects, features and advantages of the present disclosure can also be derived from the examples of embodiments to be described hereinafter and are explained with reference to examples of embodiments. The present disclosure will be described in more detail hereinafter with reference of examples of embodiments but to which the present disclosure is not limited.

DETAILED DESCRIPTION OF THE INVENTION

Figure 1:
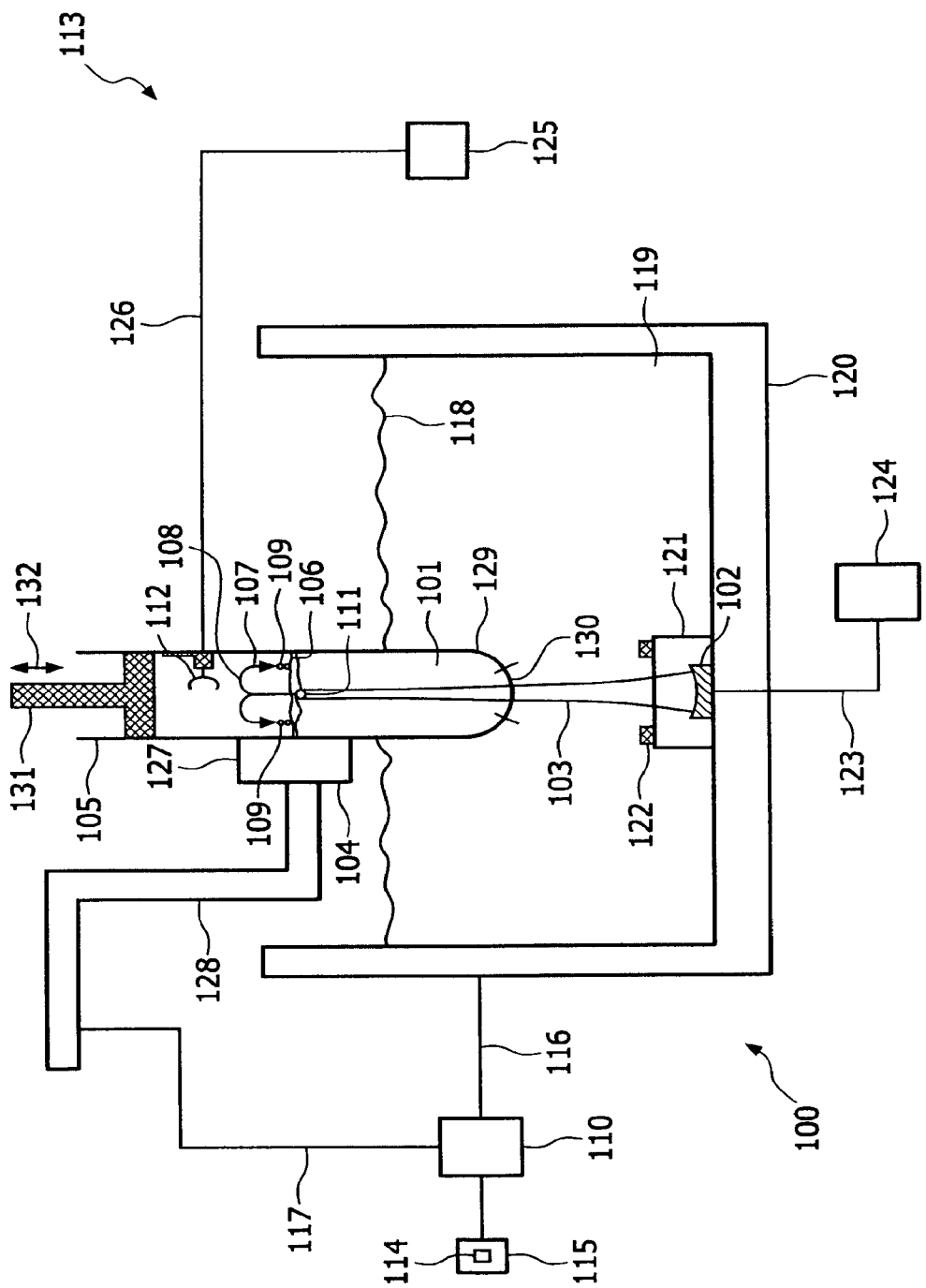
FIG. 1 schematically shows a system for irradiating a liquid sample with acoustic energy to generate cavitation according to an exemplary embodiment of the present disclosure.

Similar or relating components in the several figures are provided with the same reference numerals. The view in the figure is schematic and not fully scaled.

FIG. 1 shows an apparatus 100 for irradiating a liquid sample 101 with acoustic energy to generate cavitation in the liquid sample. The shown apparatus comprises a source 102 for emitting high intensity ultrasound waves 103. Furthermore a receiving section 104 for receiving a cartridge 105 is shown. In this exemplary embodiment of the present disclosure the receiving section 104 is embodied as a fixation element 127 at which the cartridge 105 can be fixed and subsequently be positioned in a desired position. This position might be arranged in such a way, that the apparatus focuses the high intensity ultrasound waves 103 on the liquid air interface 106 when the cartridge is inserted into the receiving section.

It is clearly shown in FIG. 1, that the focus position 111 is positioned at the liquid air interface 106. By focusing the acoustic energy onto the liquid air interface or sufficiently close to the liquid air interface and by using sufficiently high powers for the transducer 102 a fountain 108 of liquid is created by the HIFU waves. As shown in FIG. 1 the fountain has been developed within the cartridge and above the liquid air interface. Droplets 109 of the fountain falling back from the fountain onto the liquid sample are nucleation elements 107 for reducing a minimum power necessary for generating cavitation in the liquid. The fountain droplets 109 returning to the sample are able to induce cavitation. The droplets 109 may introduce small air bubbles and/or air films which in turn are the starting point for a cavitation.

In other words this exemplary embodiment of the present disclosure avoids focusing close to the cartridge wall 129 which may avoid melting and/or degradation of the cartridge material. But also the reduced power may avoid melting and/or degradation of the cartridge material. Consequently a polymer based cartridge which may be part of a sample-in result-out consumable system is possible. Furthermore as the minimum power necessary for generating cavitation is reduced mixing and lysing can be subsequently done in one single cartridge without having the need to substantially change the used power of the source 102. In other words it may be avoidable to have to use a glass container for the sample. That is because heterogeneous cavitation is induced by HIFU via the fountain in contrast to known technologies using homogeneous cavitation. The HIFU waves may for example be in the MHz-range.

As the minimum power necessary for generating cavitation is reduced by this exemplary embodiment of the present disclosure smaller transducers may be used which corresponds to a miniaturization possibility of the apparatus. Thus the apparatus offers the possibility to transfer the HIFU waves 103 across a dry interface 130 for example being an acoustic window made out of an elastic foil. Furthermore a possibility to use polymer based cartridge materials within the system 113 comprising the apparatus 100 and the cartridge 105 corresponds to a cost reduction of measurements done with the system 113 and may correspond to an increased ecological compatibility as less energy may be needed for an average measurement with the apparatus.

Furthermore a computer 115 is shown with a computer program element 114 stored on the computer which computer may be adapted to cause a focusing onto the liquid-air interface 106 via the control unit 110. The control unit may via leads 117 control the positioning system 128 in order to match the focus position 111 with the liquid air interface 106 in order to generate the fountain. Furthermore a detection unit 112 for measuring a physical parameter of the liquid sample is shown within the cartridge 105. The detection unit may for example be embodied as a passive cavitation detector (PCD) which may be a piezo transducer. Via leads 126 a processing unit 125 may analyze the liquid sample based on the detected physical parameter.

Furthermore FIG. 1 shows a housing 121 for the source 102 for example in order to protect the source against a liquid coupling fluid 119. Thus this exemplary embodiment of the present disclosure shows at least partially a wet coupling of the HIFU waves from the source 102 to the cartridge 105. The housing may be fixed to the chamber 120 for the coupling medium 119 by screws 122. Nevertheless it may also be possible to generate the fountain with an apparatus using complete dry coupling without any liquid in the propagation path of the HIFU waves as described above. A plunger 131 that may limit the height above the liquid-air interface by moving the plunger along the direction 132 is shown. By moving the plunger 131 from a direct contact with the sample vertically up (upwards direction in FIG. 1) the power threshold at which cavitation in the sample sets in may decrease with increased distance of the plunger from the interface. In other words cavitation may be a function of the air volume above the liquid sample.

Possible technical equipment to which the present disclosure shall not be limited may be the following devices: PM5193: programmable synthesizer/function generator with a working range between 0.1 mHz and 50 MHz. Amplifier: ENI 240L Power Amplifier 50 dB 20 kHz-10 MHz or AR worldwide KAA204 RF Power Amplifier 50 dB 0.5-100 MHz 200 W; Tektronix TDS3014: Four Channel Color Digital Phosphor Oscilloscope; Agilent 4395A: 10 Hz-500 MHz/ 10 Hz-500 MHz/10 kHz-500 MHz Network/Spectrum/Impedance Analyzer; HiFu piezo transducer: JR20/60 supplied by Dongfang Jinrong; Passive Cavitation Detector (PCD) (piezo transducer): JR20/60, JR15/30, JR12/30 supplied by Dongfang Jinrong.

Furthermore a modified 10 ml PP syringe may be used for fountain based cavitation means. The syringe tip may be removed and a 100 um PP foil may be laser-sealed to the top side. The plunger may be used to adjust the air volume above the liquid sample. The PCD may be clamped with ultrasound gel (Aquaflex supplied by Parker Laboratries Inc) to the outside of the syringe-wall thus constituting a possible protrusion element. The PCD is used to investigate cavitation inside the syringe. A similar setup may be used to demonstrate a fountain based cavitation across a dry interface. A similar setup may be used to determine cavitation induced by a rough surface.

Figure 2:
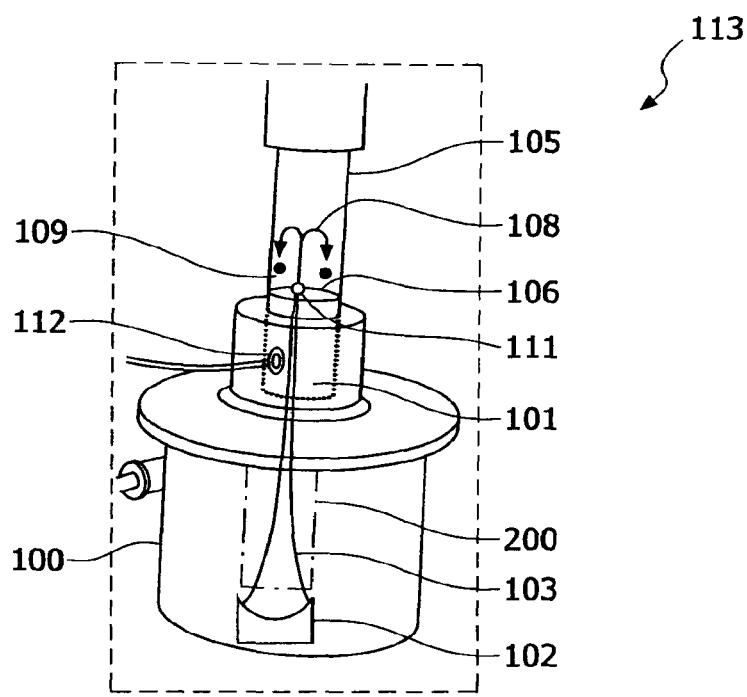
FIG. 2 schematically shows a system for irradiating a liquid sample with acoustic energy to generate cavitation in the liquid sample according to another exemplary embodiment of the present disclosure.

FIG. 2 shows another exemplary embodiment of a system 113 for irradiating a liquid sample 101 with acoustic energy to generate cavitation in the liquid sample wherein an apparatus 100 and the cartridge 105 for containing the liquid sample are comprised in the system. Furthermore the detection unit 112 is shown which is placed in the liquid sample. Furthermore the fountain 108 creating falling back droplets 109 is shown. The source 102 is arranged in combination with the position of the cartridge 105 and possibly with a lens (not shown) in such a way that the focus position 111 is positioned at the liquid air interface 106. The exemplary embodiment of the present disclosure shows a complete dry coupling of the HIFU waves 103 through a full solid coupler 200. As the minimum power necessary for generating cavitation is reduced by the fountain full solid state materials like for example polymer based materials may be used as coupling mediums as substantial heat creation or deformation in the materials transferring the HIFU energy is avoided.

Figure 3:
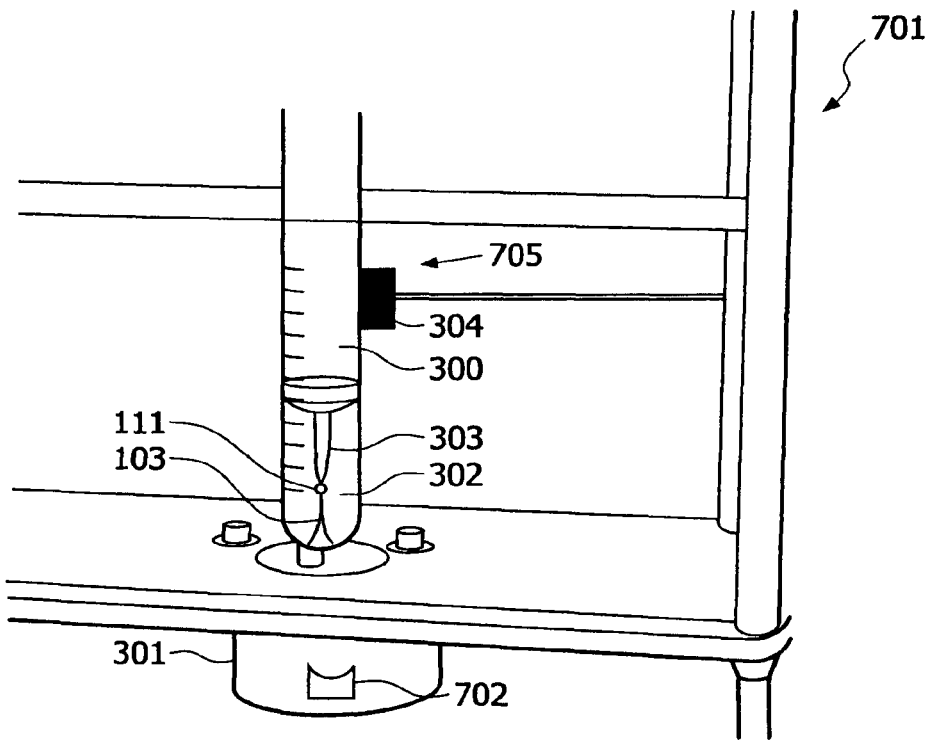
FIG. 3 schematically shows a cartridge according to another exemplary embodiment of the present disclosure.

FIG. 3 shows a cartridge 300 for an apparatus 301 for irradiating a sample with acoustic energy to generate cavitation in the liquid sample. The cartridge comprising a chamber 302 for containing the liquid sample and a nucleation element 303 fixed at the chamber. The nucleation element may for example be a ceramic element like a ceramic rod or an element made out of aluminum. Thereby the surface roughness of the nucleation element 303 may be adapted in such a way that cavitation is induced at a reduced power level compared to setups without such a nucleation element. Furthermore the material to be used for the nucleation element is chosen in such a way that it resists the HIFU wave power in or near the focal spot 111 sufficiently long to complete a test done with the system 701. The system 701 comprises the apparatus 301 which itself comprises the source 702. Furthermore a receiving section 705 comprised by the apparatus is shown. Thereby the receiving section is embodied as a fixation element 304 at which the cartridge 300 can be fixed in order to position it in such a way that the apparatus focuses the HIFU waves on or close to the nucleation element when the cartridge is inserted into the receiving section.

Figure 4:
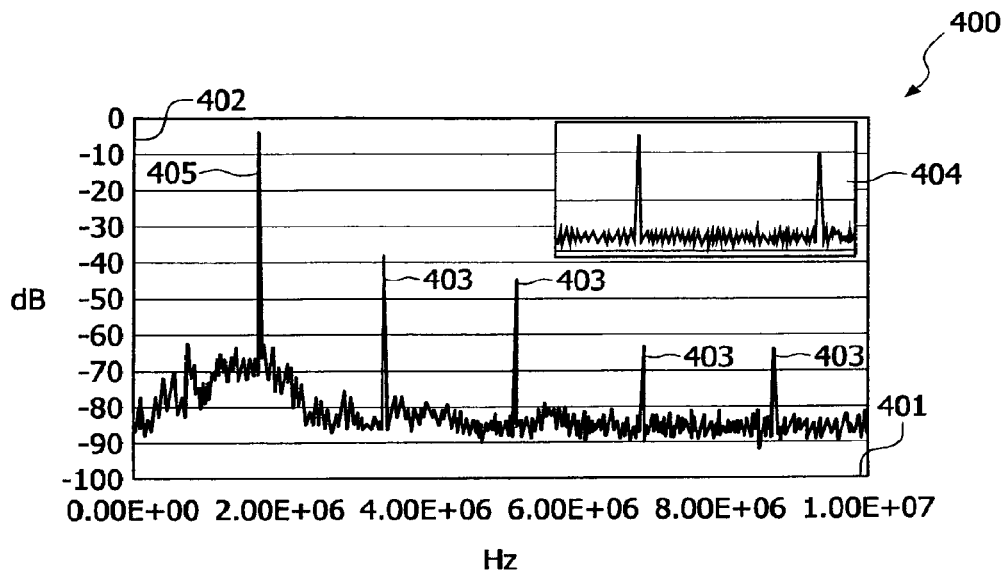
FIG. 4 schematically shows a frequency spectrum obtained with a passive cavitation detector.

FIG. 4 shows a frequency spectrum obtained with a passive cavitation detector (PCD) that is inserted in a cartridge in which cavitation is induced by a fountain or a nucleation element as described above. The insert 404 shows a spectrum without cavitation. The x-coordinate 401 displays the frequency in Hz wherein the y-coordinate 402 displays in decibel a magnitude of the measured power by the PCD relative to a specified reference level. Thereby insert 404 reflects only left part of spectrum 401. The sharp peaks in both 401 and 404 are respectively the base frequency 405 at 1.7 MHz and the overtone(s) 403. The broadband signal present in 401 evidenced the presence of cavitation.

Figure 5:
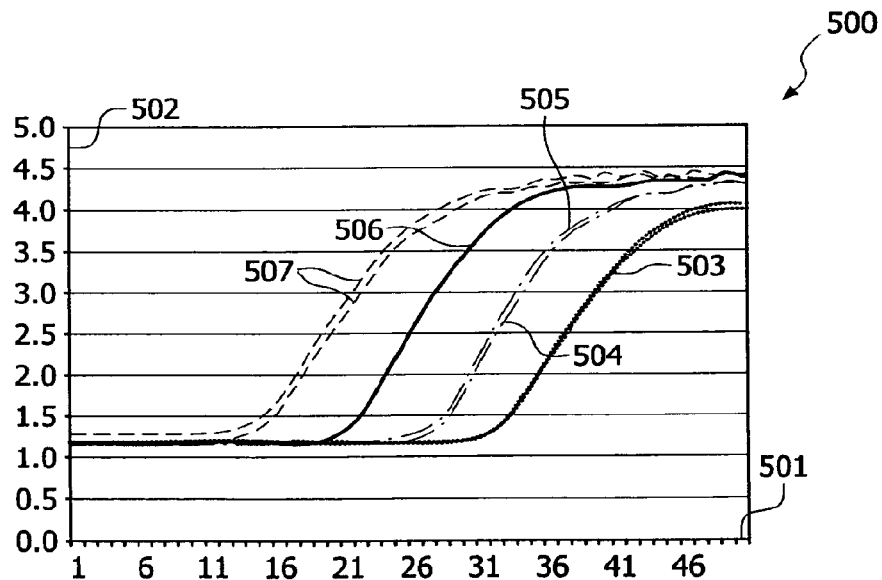
FIG. 5 schematically shows a diagram depicting HIFU effect on candida albicans cells.

FIG. 5 shows a diagram 500 wherein the x-coordinate 501 displays a cavitation value which cavitation value shall herewith defined as number of PCR cycles. Furthermore the y-coordinate 502 displays the relative fluorescent units (RFU) value. The curves 503, 504, 505, and 506 show the effect of HIFU on candida albicans cells. 503 shows PCR curves (duplicates) for untreated cells, 506 shows cells treated with glass beads wherein 504 and 505 show results from cells exposed to heat. In contrary to that 507 displays the result of cells exposed to HIFU according to the present disclosure. Thus FIG. 5 discloses that compared to the present gold standard heating has a six unit higher Ct value (defined below) and lysis with the present disclosure has a six unit lower Ct value wherein it shall explicitly be noted that a lower Ct value has several advantages.

In the following the term CT value and the advantages of a lower Ct value shall be described. The Ct value is the PCR-cycle-number the detected signal passes a pre-set RFU-value. Low Ct means that a low number of multiplication steps are required to pass the threshold. In other words low Ct value corresponds with high initial DNA concentration and consequently with very effective lysis that is done in case of the present disclosure with HIFU. In other words the present disclosure may overcome the gold standard with a factor of $2^6=64$.

Figure 6:
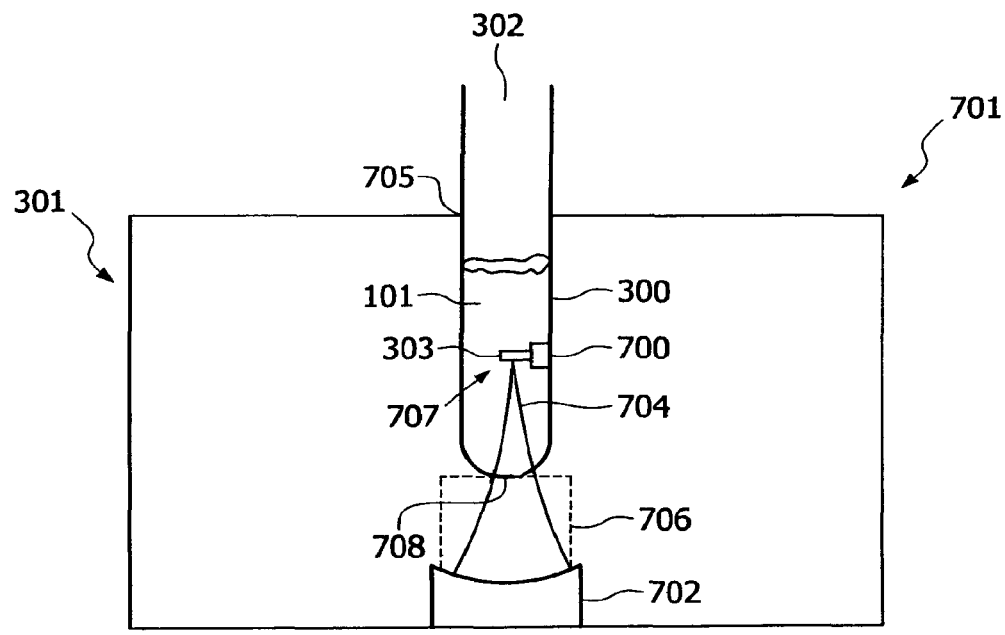
FIG. 6 schematically shows a system for irradiating a liquid sample with acoustic energy to generate cavitation in the liquid sample according to another exemplary embodiment of the present disclosure.

FIG. 6 shows another exemplary embodiment of the present disclosure in which a system 701 for irradiating a liquid sample with acoustic energy to generate cavitation in the liquid sample. The system comprises an apparatus 301 and a source 702 for emitting the HIFU waves 704. The system further comprises a cartridge 300 wherein the cartridge contains the liquid sample 101. The apparatus 300 further comprises a receiving section 705 for receiving the cartridge. The receiving section may thereby be any element or part of the apparatus at which physical contact with the cartridge is established when inserting the cartridge into the apparatus.

Thereby the apparatus 301 focuses the HIFU waves on the nucleation element 303 when the cartridge is inserted into the receiving section. Furthermore the cartridge comprises a chamber 302 for containing the liquid sample and comprises a nucleation element 303 fixed at the chamber. To fix the nucleation element adequately a protrusion element 700 is comprised within the cartridge in order to fix the nucleation element at the cartridge in. Thereby the protrusion element may be embodied in this and in any other embodiment of the present disclosure by any device being able to hold and fix the nucleation element in such a way, that the nucleation element extends into the liquid sample and the focus position 707 can be positioned at or close to the nucleation element 303.

This exemplary embodiment of the present disclosure can be used in a setup with complete dry coupling in which a full solid coupler 706 which is comprised by the system 701. For example polymer based materials may be used to couple the HIFU waves from the source to the cartridge. In addition to that a dry interface 708 which may be embodied as an acoustic window can be used with this exemplary embodiment of the present disclosure as an reduced minimum power for cavitation can be realized and thus heating or leakage of material of the cartridge can may be avoided.

Figure 7:
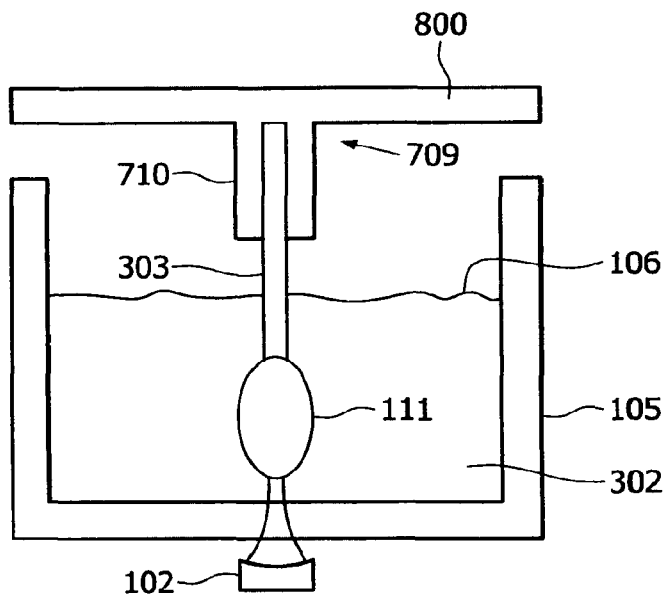
FIG. 7 schematically shows a cartridge with a nucleation element according to another exemplary embodiment of the present disclosure.

FIG. 7 schematically shows an embodiment of a cartridge 105 with at least one nucleation element 303 protruding from the ceiling 800. The protruding is realized by the protrusion element 709 being embodied as a clamp 710 clamping the nucleation element 303. The ceiling may be part of the cartridge but may also be a physically separated element. Dependent on the diameter of the nucleation element and the diameter of the focal spot or focal zone 111 of the source 102 the nucleation element may be in line with the vertical axis of the focal zone but may also be placed off-centered. The protrusion element 709 of the cartridge realizes a vertical fixation of the nucleation element. But also horizontal, inclined, centered or uncentered fixations by the protrusion element are possible. It shall explicitly be noted that this type of cavitation induction could be used independent from the focusing on the liquid-air interface and the formation of a fountain.

Figure 8:
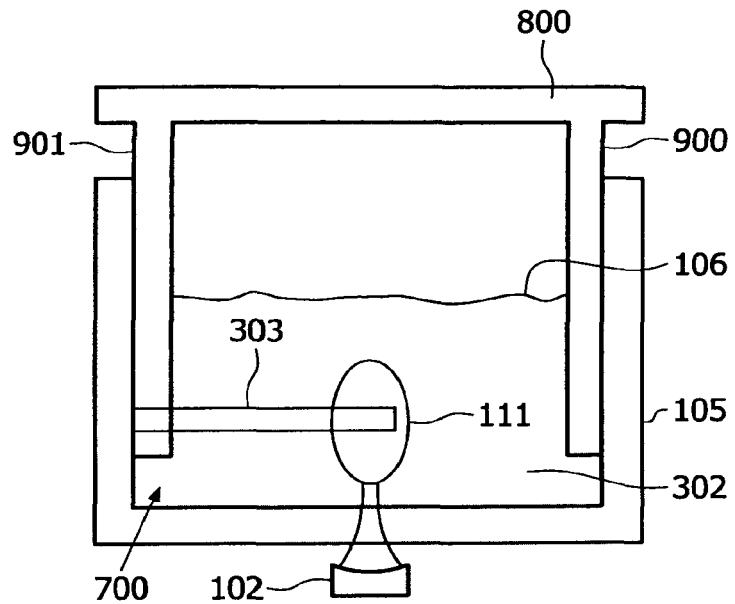
FIG. 8 schematically shows a cartridge with a nucleation element according to another exemplary embodiment of the present disclosure.

FIG. 8 schematically shows another embodiment of a cartridge 105 with at least one nucleation element 303. The ceiling 800 has two side walls 900 and 901. In other words the cartridge comprises a protrusion element 700 as a fixation element for the nucleation element 303. Thus the nucleation element protrudes horizontally from the side-wall 901. Symbolically a source 102 emitting HIFU waves is shown. It shall again explicitly be noted that this type of cavitation induction could be used independent from the focusing on the liquid-air interface and the formation of a fountain.

Figure 9:
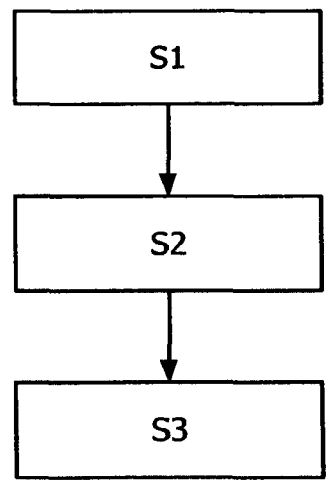
FIG. 9 shows a flow diagram illustrating a method according to another exemplary embodiment of the present disclosure.

FIG. 9 shows a flow diagram of a method according to an exemplary embodiment of the present disclosure wherein the method comprises the steps S1 providing for a source for emitting high intensity ultrasound waves and S2 providing for a cartridge containing the liquid sample and a liquid air interface within the cartridge. In a third step S3 a focusing of the emitted high intensity ultrasound waves on the liquid air interface within the cartridge is done. By focusing the HIFU waves onto the liquid air interface out of liquid from the liquid sample is generated which causes droplets falling back into the sample and reducing the power threshold at which cavitation sets in within the liquid sample. Both FIGS. 7 and 8 show cartridges with nucleation elements like e.g. a ceramic rod or an aluminum nucleation element by which the power threshold for cavitation in the sample within the chamber 302 may be reduced. A rough surface of theses nucleation element may be the source of small air-bubbles when the HIFU waves are focused onto them, which bubbles in turn may act as nucleation sites.

Other variations to the disclosed embodiments can be understood and effected by those skilled in the art and practicing the claims, from the studying of the drawings, the disclosure, and the appendant claims. In the claims the word comprising does not exclude other elements or steps and the indefinite article "a" or "an" does not exclude a plurality. A single processor or other units may fulfill the function of several items or steps recited in the claims. The mere effect that certain measurements are recited in mutually different dependent claims does not indicate that a combination of these measures cannot be used to advantage. A computer program may be stored/distributed on a suitable medium such as an optical storage medium or a solid state medium supplied together with or as part of other hardware, but may also be distributed in other forms such as via the internet or other wire or wireless telecommunication systems.

Having described the invention, the following is claimed:

1. A system for irradiating a liquid sample with acoustic energy to generate cavitation in the liquid sample, the system comprising:
   a cartridge having a chamber for containing the liquid sample;
   a nucleation element extending at least partially into the chamber of the cartridge, said nucleation element having a rough surface to generate a source of air bubbles that act as nucleation sites within the liquid sample contained in the chamber;
   an apparatus including:
      a receiving section for receiving the cartridge;
      a source for emitting high intensity ultrasound waves into the cartridge; and
      a control unit for causing the high intensity ultrasound waves to be focused on a focus position within the liquid sample in the chamber, said focus position at or near the nucleation element extending at least partially into the chamber of the cartridge; and
   a focusing element to focus the high intensity ultrasound waves at said focus position within the liquid sample.

2. The system according to claim 1, wherein the cartridge further comprises a protrusion element for locating at least a portion of the nucleation element at or near said focus position within the liquid sample.

3. The system according to claim 2, wherein said protrusion element is located within the chamber of said cartridge.

4. The system according to claim 2, wherein said protrusion element is a clamp for holding the nucleation element.

5. The system according to claim 2, wherein said system further comprises a lid to cover at least a portion of an opening to the chamber of said cartridge.

6. The system according to claim 5, wherein said lid forms a portion of the cartridge.

7. The system according to claim 5, wherein said protrusion element is attached to the lid.

8. The system according to claim 7, wherein said protrusion element is a clamp.

9. The system according to claim 5, wherein said lid includes a side wall, said protrusion element extending from the side wall.

10. The system according to claim 9, wherein said nucleation element extends horizontally from the side wall.

11. The system according to claim 1, wherein said nucleation element is comprised of a ceramic element.

12. The system according to claim 1, wherein said nucleation element is comprised of aluminum.

13. The system according to claim 1, wherein said nucleation element is aligned with a vertical axis of said focus position within the liquid sample.

14. The system according to claim 1, wherein said nucleation element is attached to said cartridge.

15. The system according to claim 1, wherein the system further comprises a completely dry coupler for transferring the high intensity ultrasound waves into the cartridge when the cartridge is received in the receiving section.

16. The system according to claim 1, wherein the system further comprises a fully solid coupler for at least partially transferring the high intensity ultrasound waves from the source to the cartridge.

17. The system according to claim 1, wherein the focusing element includes a lens.

18. The system according to claim 1, wherein said system further comprises a three-dimensional positioning system controlled by said control unit, wherein the three-dimensional positioning system positions the cartridge relative to the source.

19. The system according to claim 1, wherein said control unit adjusts at least one of the following parameters: power level of the source, the focus position, and shape of a focal spot associated with the focus position.

* * * * *